(12) United States Patent
Harada et al.

(10) Patent No.: US 6,822,083 B1
(45) Date of Patent: Nov. 23, 2004

(54) TSA305 GENE

(75) Inventors: Yosuke Harada, Tokushima (JP); Kouichi Ozaki, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/555,367

(22) PCT Filed: Nov. 25, 1998

(86) PCT No.: PCT/JP98/05306

§ 371 (c)(1),
(2), (4) Date: May 30, 2000

(87) PCT Pub. No.: WO99/28457

PCT Pub. Date: Jun. 10, 1999

(30) Foreign Application Priority Data

Nov. 28, 1997 (JP) ............................................. 9-343789
Apr. 20, 1998 (JP) ........................................... 10-126803

(51) Int. Cl.$^7$ .............................................. C07H 21/04
(52) U.S. Cl. ................... 536/23.5; 536/23.1; 536/24.33
(58) Field of Search ............................. 536/23.1, 23.5, 536/24.33; 530/350, 387.1

(56) References Cited

FOREIGN PATENT DOCUMENTS

| WO | WO98/56804 | 12/1998 |
| WO | WO 99 24463 | 5/1999 |
| WO | WO99/27088 | 6/1999 |

OTHER PUBLICATIONS

Burgess et al., J of Cell Bio. 111:2129–2138, 1990.*
Lazar et al. Molecular and Cellular Biology 8:1247–1252, 1988.*
Bowie et al. Science, 247:1306–1310, 1990.*
Alberts et al., Molecular Biology of the Cell, 3rd edition, 1994, p. 465.*
Grant et al., *The Caenorhabditis elagans sel–1 Gene, a Negative Regulator of lin–12 and glp–1, Encodes a Predicted Extracellular Protein*, Feb. 2, 1996, pp. 237–247.
Grant, et al., *Structure, function, and expression of SEL–1, a negative regulator of LIN–12 and GLP–1 in C. elegans*, Development, Feb. 1997, vol. 124 (3) pp 17–24.
International Search Report dated Mar. 3, 1999.
Harada et al. *J. of Human Genetics*, 44(5):330–336 (1999) full article considered.

* cited by examiner

*Primary Examiner*—Lrry R. Helms
*Assistant Examiner*—Misook Yu
(74) *Attorney, Agent, or Firm*—Sughrue Mion, PLLC

(57) ABSTRACT

The invention provides a pancreas-specific gene comprising a base sequence coding for the amino acid sequence shown under SEQ ID NO:1, which gene is effective particularly in the fields of study, diagnosis and treatment, among others, of pancreatic carcinoma.

3 Claims, 3 Drawing Sheets

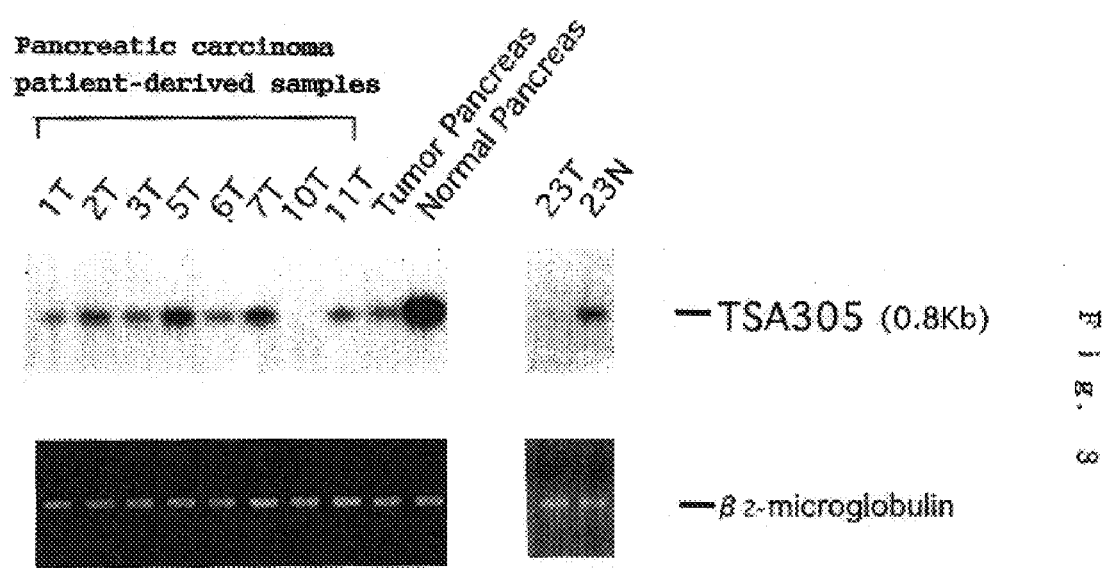

TSA305 GENE

TECHNICAL FIELD

The present invention relates to a gene, named TSA305, coding for a protein specifically expressed in the pancreas and, more particularly, to the above pancreas-specific gene having a high level of homology with nematode sel-1 and expected to show an anticancer activity. The invention also relates to a novel protein encoded by such gene and to a specific antibody thereto.

BACKGROUND ART

Pancreatic cancer holds the fourth and fifth place on the list of cancer-related deaths in Japan and western countries, respectively and has the worst prognosis among digestive system malignancies (Poston, J. G., et al., Gut, 32, 800–812 (1991)). The ultimate goal in cancer research is to discriminate early stage gene changes leading to malignant transformation. If such changes can be differentiated, genetic tools for early diagnosis may possibly be developed and novel therapeutic approaches for more effective treatment of this lethal disease will possibly be taken.

Meanwhile, the nematode sel-1 gene reportedly has an inhibitory action on Notch/lin-12 which suppresses the differentiation of ectoderm into neuroblast in neural development in nematodes (Genetics, 143 (1), 237–247 (1996); Development, 124 (3), 637–644 (1997)). Said Notch/lin-12, when forcedly expressed, causes breast cancer or leukemia and therefore is considered to be a cancer-related gene. The above sel-1 gene suppressively acting on said cancer-related gene is therefore considered to suppressively act on cancer as well. At present, however, the roles of these genes have not been fully elucidated.

Elucidation of the physiological roles of such genes and the information obtained therefrom are important in elucidating the mechanisms of onset of diseases such as malignant transformation and inflammation and are desired not only in the field of basic scientific studies but also in the pharmaceutical field in determining the causes of such diseases as cancer and inflammation and developing treatment methods for such diseases.

DISCLOSURE OF INVENTION

The present invention has for its object to provide the above information desired in the relevant field of art, in particular a gene coding for a novel protein homolog and having homology with the sel-1 gene.

With that object in view, the present inventors made an arduous search among genes derived from various human tissues and, as a result, succeeded in newly isolating and identifying a gene coding for a protein specifically expressed in the pancreas and found that the above object can be realized with said gene. As a result, the present invention has now been completed.

Thus, the present invention provides a pancreas-specific gene, TSA305, comprising a nucleotide sequence coding for a protein having the amino acid sequence shown under SEQ ID NO:1, in particular the TSA305 gene which is a human gene.

The invention also provides a pancreas-specific protein (TSA305 protein) comprising the amino acid sequence shown under SEQ ID NO:1 and an antibody capable of coupling therewith.

The invention further provides a pancreas-specific gene, TSA305, which is a polynucleotide defined below under (a) or (b) in particular to the TSA305 gene which is a human gene:

(a) A polynucleotide comprising the whole or part of the nucleotide sequence shown under SEQ ID NO:2.

(b) A polynucleotide capable of hybridizing with a DNA having the nucleotide sequence shown under SEQ ID NO:2 under stringent conditions.

In addition, the present invention provides the above gene in DNA fragment form which is useful as a specific probe or specific primer for gene detection.

In expressing amino acids, peptides, nucleotide sequences, nucleic acids and the like by abbreviations or symbols in the following, the nomenclature of the IUPAC-IUB [IUPAC-IUB Communication on Biological Nomenclature, Eur. J. Biochem., 138: 9 (1984)], the "Guideline for preparing specifications etc. containing nucleotide sequences or amino acid sequences" (edited by the Patent Office of Japan) and the conventional symbols in the relevant field are followed or used.

As a specific example of the gene of the invention, there may be mentioned the one deduced from the DNA sequence of a PCR product named "TSA305" which is to be shown later in the example section. The nucleotide sequence thereof is as shown under SEQ ID NO:3.

Said gene is a human cDNA containing a coding region having the nucleotide sequence shown under SEQ ID NO:2 and coding for a novel pancreas-specific protein (hereinafter referred to as TSA305 protein) composed of 794 amino acid residues as shown under SEQ ID NO:1 and is composed of a total length of 7,885 nucleotides.

As a result of searching in the GenBank/EMBL database utilizing the FASTA program (Person, W. R., et al., Proc. Natl. Acad. Sci. USA, 85, 2444–2448 (1988)), it was confirmed that the product of expression of the TSA305 gene of the invention, namely the TSA305 protein, has a very high level of homology with the nematode sel-1 gene (cf. the reference cited above). In view of this fact, it is considered that the gene of the invention, like the above-mentioned sel-1, act suppressively on Notch/lin-12 which is a cancer-related gene considered to be involved in embryogenesis in general.

The locus of the gene of the invention is q24.3-q31.1 of the 14th chromosome where a gene causative of insulin-dependent diabetes mellitus (IDDM) is considered to exist. In view of this fact, it is strongly suggested that the gene of the invention be related with diabetes.

It was further revealed that the product of expression of the gene of the invention is a protein containing a fibronectin type II collagen binding domain. Such collagen binding site close to the N terminal suggests involvement of the protein in fibrogenesis and, based on this, it is strongly suggested that the gene of the invention be involved in fibrosis.

In addition, since all of the pancreatic carcinoma preparations tested showed a failure of expression of the gene of the invention and the gene is expressed mainly in normal pancreases, it is suggested that the gene of the invention be potentially valuable in forecasting malignant transformation.

Thus, information and means very useful in elucidating, understanding, diagnosing, preventing and treating various diseases such as mammary cancer, leukemia, fibrosis, diabetes and pancreatic carcinoma, in particular pancreatic carcinoma, are given as a result of providing the TSA305 gene and the product of its expression according to the present invention. The gene of the invention can judiciously be used also in developing a novel drug inducing the expression of the gene of the invention which is utilizable in the treatment of various diseases such as mentioned above. Furthermore, detection of the expression of the gene of the invention or the product of its expression in an individual animal or a specific tissue or detection of a mutation (deletion or point mutation) of said gene or abnormal expression thereof, for instance, is considered to be utilizable adequately in elucidating or diagnosing the above diseases.

The gene of the invention is specifically represented by a gene containing a nucleotide sequence coding for a protein having the amino acid sequence shown under SEQ ID NO:1 or a gene which is a polynucleotide containing the nucleotide sequence shown under SEQ ID NO:2. However, the gene of the invention is not particularly limited to these but may be, for example, a gene leading to a certain modification in the above specific amino acid sequence or a gene having a certain level of homology with the above specific nucleotide sequence.

Thus, the gene of the invention also includes a gene containing a nucleotide sequence coding for a protein having an amino acid sequence derived from the amino acid sequence shown under SEQ ID NO:1 by deletion, substitution or addition of one or a plurality of amino acid residues and having the same activity as that of TSA305. The extent and site(s) of "deletion, substitution or addition of an amino acid residue or residues" are not particularly restricted if the modified protein is a product of the same effect which has the same function as the protein having the amino acid sequence shown under SEQ ID NO:1. The term "plurality" used above means 2 or more, normally several.

While the modification (mutation) or the like of the above amino acid sequence may occur naturally, for example by mutation or posttranslational modification, artificial modification is also possible based on a nature-derived gene (for example, a specific example of the gene of the present invention). The present invention covers all modified genes having the above characteristic without reference to the cause and means, among others, of such modification or mutation.

As examples of the above artificial means, there may be mentioned site-specific mutagenesis [Methods in Enzymology, 154: 350, 367–382 (1987; ibid., 100: 468 (1983); Nucleic Acids Res., 12: 9441 (1984); Zoku Seikagaku Jikken Koza (Experiments in Biochemistry, second series) 1: "Idensi Kenkyuho (Methods in Gene Research) II", edited by the Biochemical Society of Japan, p. 105 (1986)] and other genetic engineering techniques, means of chemical synthesis such as the phosphotriester method or phosphoamidite method [J. Am. Chem. Soc., 89: 4801 (1967): ibid., 91: 3350 (1969); Science, 1: 178 (1968); Tetrahedron Lett., 22: 1859 (1981); ibid., 24: 245 (1983)], and combinations thereof.

In a mode of embodiment of the gene of the present invention, there may be mentioned a gene which is a polynucleotide containing the whole or part of the nucleotide sequence shown under SEQ ID NO:3. The open reading frame (nucleotide sequence shown under SEQ ID NO:2) containing in this nucleotide sequence also serves as an example of combination of codons specifying respective amino acid residues in the above amino acid sequence (SEQ ID NO:1). The gene of the invention is not limited to this but can of course have a nucleotide sequence in which an arbitrary combination of codons is selected. The selection of codons can be made in the conventional manner, for example the codon usage in the host employed, among others, can be taken into consideration [Nucleic Acids Res., 9: 43 (1981)].

While the gene of the invention is represented in terms of single strand DNA nucleotide sequence, as shown, for example, under SEQ ID NO:2, the invention of course includes a polynucleotide having a nucleotide sequence complementary to such nucleotide sequence, or a component comprising both of these as well. It is not limited to a DNA such as a cDNA.

Furthermore, as mentioned above, the gene of the invention is not limited to a polynucleotide containing the whole or part of the nucleotide sequence shown under SEQ ID NO:2, but includes genes comprising a nucleotide sequence having a certain level of homology with said nucleotide sequence as well. As such genes, there may be mentioned those at least capable of hybridizing with a DNA comprising the nucleotide sequence shown under SEQ ID NO:2 under such stringent conditions as mentioned below and incapable of being released therefrom even by washing under certain conditions.

Thus, mention may be made, as an example, of a gene having a nucleotide sequence which hybridizes with a DNA having the nucleotide sequence shown under SEQ ID NO:2 under conditions: at 65° C. overnight in 6×SSC or at 37° C. overnight in 4×SSC containing 50% formamide and is not released from said DNA under washing conditions: 30 minutes at 65° C. with 2×SSC. Here, "SSC" means standard saline citrate; 1×SSC =0.15 M NaCl, 0.015 M sodium citrate).

The gene of the present invention can be produced and recovered with ease by general genetic engineering techniques [see, for example, Molecular Cloning, 2nd Ed., Cold Spring Harbor Lab. Press (1989); Zoku Seikagaku Jikken Koza (Experiments in Biochemistry, second series) "Idensi Kenkyuho (Methods in Gene Research) I, II and III", edited by the Biochemical Society of Japan (1986)] based on the information on the sequence of a typical example thereof.

Specifically, the production/recovery can be carried out by constructing a cDNA library in the conventional manner from an appropriate origin in which the gene of the invention is expressed and selecting a desired clone therefrom using an appropriate probe or antibody specific to the gene of the invention [Proc. Natl. Acad. Sci. USA, 78: 6613 (1981); Science, 222: 778 (1983)].

As examples of the origin of cDNA in the above process, there may be mentioned various cells and tissues in which the gene of the invention is expressed, cultured cells derived therefrom and the like, in particular the pancreatic tissue. Isolation of total RNA from these, isolation and purification of mRNA, obtainment of cDNA and cloning thereof, among others, can all be performed in the conventional manner. cDNA libraries are also commercially available and such cDNA libraries, for example various cDNA libraries commercially available from Clontech Lab. Inc. can also be used in the practice of the present invention.

The method of screening the cDNA library for the gene of the invention is not particularly restricted but may be a conventional one. As specific examples, there may be mentioned the method comprising selecting the corresponding cDNA clone by immunological screening using a specific antibody to the protein produced by the cDNA, plaque hybridization or colony hybridization using a probe selectively binding to the desired DNA sequence, and combinations of these.

As examples of the probe to be used here, there may generally be mentioned DNAs chemically synthesized based on the information on the nucleotide sequence of the gene of the invention, among others. Of course, it is also possible to successfully utilize the gene of the invention already obtained as such or fragments thereof.

The screening for the gene of the invention can also be made by the protein interaction cloning procedure using the TSA305 protein in lieu of the above specific antibody and, further, the screening method comprising using, as a screening probe, a sense or antisense primer designed based on the information on the nucleotide sequence of the gene of the invention can also be employed.

In accordance with the present invention, the mRNA expression levels in cells under different conditions or a plurality of different cell groups can be directly compared and investigated by the differential display technique (Liand, P., et al., Science, 257: 967–971 (1992)).

In obtaining the gene of the present invention, DNA/RNA amplification by the PCR technique [Science, 230: 1350 (1985)] can judiciously be utilized. In particular, in cases where it is difficult to obtain the full-length cDNA from a library, the RACE technique (rapid amplification of cDNA ends; Jikken Igaku (Experimental Medicine), 12 (6): 35 (1994)), in particular the 5'-RACE technique [Proc. Natl. Acad. Sci. USA, 85: 8998 (1988)], for instance, is judiciously employed. The primers to be used when such PCR technique is employed can be adequately designed based on the information on the sequence of the gene of the invention as revealed by the present invention and can be synthesized in the conventional manner.

The amplified DNA/RNA fragments can be isolated and purified in the conventional manner, as mentioned above, for example by gel electrophoresis.

The gene of the invention or various DNA fragments obtained in the above manner can be sequenced in the conventional manner, for example by the dideoxy method [Proc. Natl. Acad. Sci. USA, 74: 5463 (1977)] or the Maxam-Gilbert method [Methods in Enzymology, 65: 499 (1980)] or, in a simple and easy manner, by using a commercial sequencing kit or the like.

By utilizing the gene of the present invention, it is possible to readily produce the corresponding gene product stably in large amounts by using general genetic engineering techniques. Therefore, the present invention also provides a vector (expression vector) containing the TSA305 gene of the invention, host cells transformed with said vector and a method of producing the TSA305 protein which comprises cultivating said host cells.

The production method can be carried out according to the ordinary recombinant DNA technology [see, for example, Science, 2: 1431 (1984); Biochem. Biophys. Res. Comm., 130: 692 (1985); Proc. Natl. Acad. Sci. USA, 80: 5990 (1983); and the references cited above].

Both prokaryotes and eukaryotes can be used as the host cells mentioned above. As prokaryotic hosts, there may be mentioned a wide variety of ones in general use, such as *Escherichia coli, Bacillus subtilis*, etc., and preferred examples are those included among *Escherichia coli* strains, in particular the *Escherichia coli* K 12 strain. The eukaryotic host cells include vertebrate cells and yeast cells, among others. As the former, COS cells [Cell, 23: 175 (1981)], which are simian cells, chinese hamster ovary cells and the dihydrofolate reductase-deficient strain thereof [Proc. Natl. Acad. Sci. USA, 77: 4216 (1980)], for instance, are judiciously used and, as the latter, yeast cells belonging to the genus Saccharomyces and the like are judiciously used. Of course, the host cells are not limited to these.

Where prokaryotic cells are used as the host, an expression plasmid can judiciously be used which is constructed using a vector capable of replicating in said host cells and providing this vector with a promoter and the SD (Shine and Dalgarno) sequence upstream of the gene of the invention and further with an initiation codon (e.g. ATG) necessary for the initiation of protein synthesis so that the gene of the invention may be expressed. Often used as the above vector are generally *Escherichia coli*-derived plasmids, for example pBR322, pBR325, pUC12 and pUC13. The vector is not limited to these, however, but various known vectors may be utilized. As commercially available vectors of the above kind which can be used in expression systems in which *Escherichia coli* is used, there may be mentioned, for example, pGEX-4T (Amersham Pharmacia Biotech), pMAL-C2, pMAl-P2 (New Englans Biolabs), pET21, pET21/lacq (Invitrogen) and pBAD/His (Invitrogen).

As the expression vector in the case of vertebrate cells being used as the host, there may be mentioned one generally having a promoter located upstream of the gene of the invention which is to be expressed, an RNA splicing site, a polyadenylation site and transcription termination sequence. When necessary, this may further have an origin of replication. As specific examples of said expression vector, there may be mentioned pSV2dhfr having the early promoter of SV40 [Mol. Cell. Biol., 1: 854 (1981)] and the like. In addition to the above, various known commercial vectors can also be used. As commercial vectors of such kind which are to be utilized in expression systems in which animal cells are used, there may be mentioned, among others, vectors for animal cells, such as pEGFP-N, pEGFP-C (Clontech), pIND (Invitrogen) and pcDNA3.1/His (Invitrogen), and vectors for insect cells, such as pFastBac HT (Gibco BRL), pAcGHLT (PharMingen), pAc5/V5-His, pMT/V5-His and pMT/Bip/V5-His (the latter three: Invitrogen).

As specific examples of the expression vector to be used when yeast cells are used as the host, there may be mentioned, among others, pAM82 having a promoter for the acid phosphatase gene [Proc. Natl. Acad. Sci. USA, 80; 1 (1983)] and the like. Commercial expression vectors for yeast cells include, among others, pPICZ (Invitrogen) and pPICZα(Invitrogen).

The promoter is not particularly restricted, either. When an Escherichia species is used as the host, the tryptophan (trp) promoter, lpp promoter, lac promoter, recA promoter, PL/PR promoter or the like can judiciously be utilized. When the host is a *Bacillus* species, the SP01 promoter, SP02 promoter, penP promoter or the like is preferred. As for the promoter to be used when a yeast species is the host, the pH05 promoter, PGK promoter, GAP promoter or ADH promoter, for instance, can judiciously be used. As preferred examples of the promoter to be used when animal cells are used as the host, there may be mentioned SV40-derived promoters, retrovirus promoters, and the metallothionein promoter, heat shock promoter, cytomegalovirus promoter and SRα promter.

Conventional fused protein expression vectors can also judiciously be used as the expression vector for the gene of the present invention. As specific examples of such vectors, there may be mentioned pGEX (Promega) for the expression of a protein fused with glutathione-S-transferase (GST) and the like.

The method of introducing the desired recombinant DNA (expression vector) into host cells for transforming the same is not particularly restricted, either, but various general methods can be employed. The transformant obtained can be cultivated in the conventional manner, whereby the desired TSA305 protein encoded by the gene of the present invention is expressed/produced and accumulated or secreted within or outside the transformant cells or on the cell membrane.

The medium to be used in the above cultivation can adequately be selected from among various conventional ones according to the host cells employed, and the cultivation can be conducted under conditions suited for the growth of the host cells.

The thus-obtained recombinant protein (TSA305 protein) can be isolated and purified, as desired, by various separation procedures utilizing its physical and/or chemical properties, among others [see, for example, "Seikagaku (Biochemical) Data Book II", pages 1175–1259, 1st edition, 1st printing, published Jun. 23, 1980 by Tokyo Kagaku Dojin; Biochemistry, 25 (25); 8274 (1986); and Eur. J. Biochem., 163: 313 (1987)]. As said methods, there may specifically be mentioned, for example, ordinary reconstitution treatment, treatment with a protein precipitating agent (salting out), centrifugation, osmotic shock procedure, sonication, ultrafiltration, various chromatographic techniques such as molecular sieve chromatography (gel filtration), adsorption chromatography, ion exchange chromatography, affinity chromatography and high-performance liquid chromatography (HPLC), dialysis and combinations of these. Particularly preferred among the above methods is affinity chromatography using a column to which a specific antibody to the TSA305 protein of the invention is bound.

Thus, the present invention further provides the novel TSA305 protein itself as obtained, for example, in the above manner. As mentioned hereinabove, said protein has a high level of homology with the nematode sel-1 and can produce an inhibitory effect on various kinds of cancer and therefore useful in the pharmaceutical field.

This TSA305 protein can also be utilized as an immunogen for producing an antibody specific to said protein. The component to be used here as the antigen may be the protein mass-produced by the genetic engineering techniques mentioned above or a fragment thereof, for instance. By utilizing such antigen, it is possible to obtain the desired antiserum (polyclonal antibody) or monoclonal antibody. The methods of producing said antibody are themselves well known to those skilled in the art and, in the practice of the present invention as well, these conventional methods can be followed [see, for example, Zoku Seikagaku Jikken Koza (Experiments in Biochemistry, second series) "Men-eki Seikagaku kenkyuho (Methods in Immunobiochemistry)", edited by the Biochemical Society of Japan (1986)].

Thus, for example, the animal to be immunized for obtaining antisera can be arbitrarily selected from among ordinary animals such as rabbits, guinea pigs, rats, mice and chickens, and immunization with the antigen mentioned above, blood collection and other procedures can also be carried out in the conventional manner.

The monoclonal antibody, too, can be produced in the conventional manner by producing hybrid cells from plasmocytes (immunocytes) of an animal immunized with the immunogen mentioned above and plasmacytoma cells, selecting a desired antibody-producing clone from among them, and cultivating said clone. The animal to be immunized is generally selected taking into consideration the compatibility with the plasmacytoma cells employed for cell fusion and, generally, mice or rats, among others, are advantageously used. The immunization can be conducted in the same manner as in the above-mentioned case of antisera and, if desirable, an ordinary adjuvant or the like may be used in combination.

The plasmacytoma cells to be used for cell fusion are not particularly restricted but, for example, various myeloma cells such as p3 (p3/x63-Ag8) [Nature, 256: 495–497 (1975)], p3-U1 [Current Topics in Microbiology and Immunology, 81: 1–7 (1978)], NS-1 [Eur. J. Immmunol., 6: 511–519 (1976)], MPC-11 [Cell, 8: 405–415 (1976)], SP2/0 [Nature, 276: 269–271 (1978) and the like, R210 in rats [Nature, 211: 131–133 (1979)] and the like as well as cells derived therefrom all can be used.

The fusion of the above immunocytes and plasmacytoma cells can be performed by a known method in the presence of a conventional fusion accelerator such as polyethylene glycol (PEG) or Sendai virus (HVJ) and the desired hybridomas can also be isolated in the conventional manner [e.g. Meth. in Enzymol., 73: 3 (1981); Zoku Seikagaku Jikken Koza (Experiments in Biochemistry, second series) cited above].

The desired antibody-producing cell line can be searched for and a monoclonal antibody can be derived therefrom in the conventional manner. Thus, for example, the search for an antibody-producing cell line can be carried out using the above-mentioned antigen of the present invention by various methods generally used in detecting antibodies, such as the ELISA technique [Meth. in Enzymol., 70: 419–439 (1980)], plaque technique, spot technique, agglutination reaction technique, Ouchterlony technique, and radioimmunoassay.

The antibody of the invention can be collected from the thus-obtained hybridomas, for example, by cultivating said hybridomas in the conventional manner and collecting the culture supernatant or by administering the hybridomas to an mammal compatible therewith and, after hybridoma growth, collecting the ascitic fluid. The former method is suited for obtaining a high-purity antibody while the latter method is suited for mass production of an antibody. The thus-obtained antibody can further be purified by conventional means such as salting out, gel filtration and affinity chromatography.

The thus-obtained antibody is characterized by its ability to bind to the TSA305 protein of the invention and can advantageously be utilized in the above-mentioned purification of the TSA305 protein and in assaying or discriminating the same by immunological techniques. The present invention thus provides such novel antibody as well.

Further, based on the information on the sequence of the gene of the invention as revealed by the present invention, the expression of the gene of the invention in individuals or in various tissues can be detected, for example by utilizing the whole or part of the nucleotide sequence of said gene.

Such detection can be carried out in the conventional manner, for example by RNA amplification by RT-PCR [reverse transcribed polymerase chain reaction; E. S. Kawasaki et al., Amplification of RNA. In PCR Protocol, A Guide to methods and applications, Academic Press, Inc., San Diego, 21–27 (1991)], northern blot analysis [Molecular Cloning, Cold Spring Harbor Lab. (1989)], in situ RT-PCR [Nucl. Acids Res., 21: 3159–3166 (1993)], in situ hybridization or a like technique for assaying the same on the cellular level or by the NASBA technique [nucleic acid sequence-based amplification; Nature, 350: 91–92 (1991)] or other various techniques. All can give good results.

When the RT-PCR technique is employed, the primers to be used are not limited in any way provided that they are specific to the gene of the invention and enable specific amplification of said gene alone. The sequences thereof can be adequately designed based on the genetic information according to the present invention. Generally, each may have a partial sequence comprising about 20 to 30 nucleotides.

In this way, the present invention provides DNA fragments useful as specific primers and/or specific probes in detecting the TSA305 gene according to the invention as well.

BRIEF DESCRIPTION OF DRAWINGS

FIG. 3 is a photograph, in lieu of a drawing, illustrating the results of RT-PCR analysis of pancreatic carcinoma samples and others as obtained in Example 1 (5). The results for TSA305 are shown in the upper section and the results for $\beta_2$-microglobulin as a control are shown in the lower section.

BEST MODE FOR CARRYING OUT THE INVENTION

Figure 1:
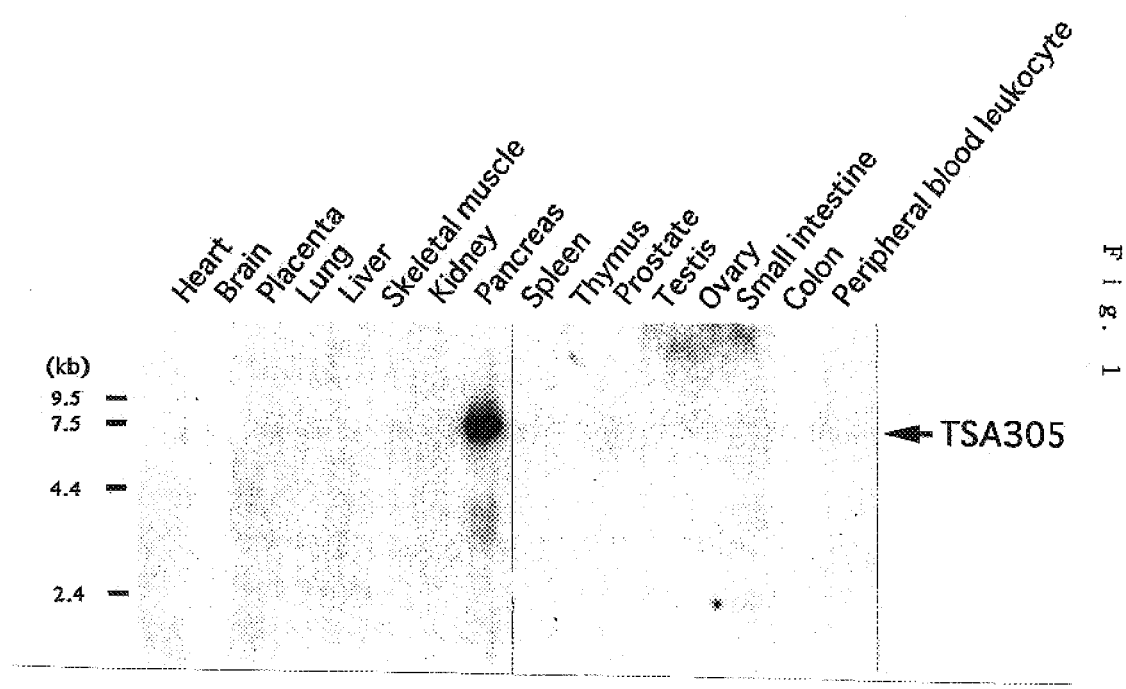
FIG. 1 is a photograph, in lieu of a drawing, illustrating the distribution of the gene of the invention in human tissues as examined by the northern blot analysis described in Example 1 under (2).

The following examples are given for illustrating the present invention in more detail.

EXAMPLE 1

(1-1) Method of Manifestation by Labeling with [$\alpha$-$^{33}$P]ATP

For identifying the human gene expressed in a tissue-specific process, the method of manifestation by labeling with [$\alpha$-$^{33}$P]ATP was used. The procedure of said method was followed essentially according to the method of Liang (Liang, P., et al., Science, 257: 967–971 (1992)), as mentioned below.

Thus, polyA RNA (0.2 $\mu$g) isolated from each of 13 human tissues (adult brain, fetal brain, lung, liver, stomach, pancreas, spleen, mammary gland, bladder, placenta, testis, kidney and heart; products of Clontech) was mixed with 25 pmol of 3'-anchored oligo-dT primer G(T)15MA (M being a mixture of G, A and C) in 8 $\mu$l of diethyl pyrocarbonate-treated water and the mixture was heated at 65° C. for 5 minutes. To this solution were added 4 $\mu$l of 5× First strand buffer (product of BRL), 2 $\mu$l of 0.1 M DTT (product of BRL), 1 $\mu$l of 250 mM dNTPs (product of BRL), 1 $\mu$l of ribonuclease inhibitor (40 units; product of Toyobo) and 1 $\mu$l of SuperScript II reverse transcriptase (200 units; product of BRL). The final volume of each reaction mixture was 20 $\mu$l. Each solution was incubated at 37° C. for 1 hour and then 2.5-fold diluted by addition of 30 $\mu$l of distilled water and the dilution was stored at −20° C. until the time of use.

cDNA was amplified by PCR in the presence of [$\alpha$-$^{33}$P] ATP-labeled (product of Amersham) 3'-anchored primer. This cDNA amplification by PCR was conducted in the following manner. Thus, 20 $\mu$l of each PCR mixture contained 2 $\mu$l of RT reaction mixture, 2 $\mu$l of 10 ×PCR buffer (product of Takara), 4 $\mu$l of 2.5 mM dNTPs, 0.25 $\mu$l of ExTaq DNA polymerase (5 units/ml; product of Takara), 25 pmol of [$\Delta$-$^{33}$P]ATP-labeled 3'-anchored oligo-dT primer and 25 pmol of 5'-primer (No. 20, decamer deoxyoligo-nucleotide primer having an arbitrary sequence, in this case the nucleotide sequence shown under SEQ ID NO:4). The PCR reaction was carried out under the following conditions. Thus, one cycle was conducted at 95° C. for 3 minutes, at 40° C. for 5 minutes and at 72° C. for 5 minutes, then 40 cycles were conducted each at 95° C. for 0.5 minutes, at 40° C. for 2 minutes and at 72° C. for 1 minute and, finally, the reaction was allowed to proceed at 72° C. for 5 minutes.

Each PCR reaction sample was extracted with ethanol and resuspended in formamide-sequencing dye and the reaction was allowed to proceed on a 6% acrylamide-7.5 M ureas sequencing gel. The gel was dried without fixation and autoradiography was carried out overnight.

(1-2) Subcloning of the Amplified cDNA Fragment

3MM filter paper with the dried gel placed thereon was marked with radioactive ink in advance. By checking the autoradiogram against this mark, the gel containing the desired cDNA-containing band was excised together with the 3MM filter paper and stirred with 300 $\mu$l of dH$_2$O for 1 hour. After removal of the polyacrylamide gel and filter paper, the cDNA was rerecovered by ethanol precipitation in the presence of 1 $\mu$l of 10 mg/ml glycogen and 0.3 M NaOAc as a carrier and redissolved in 10 $\mu$l of dH$_2$O. For reamplification, 5 $\mu$l of this solution was used. The PCR conditions and primers were the same as those in the first PCR. The reamplification product having an appropriate size was recovered as the first PCR product, and the PCR product was then cloned into the pUC118 vector (product of Takara) at the HincII site. The nucleotide sequence was determined using an ABI 377 automated sequencer (product of Applied Biosystems).

The different patterns manifested upon use of the mRNAs isolated from the 13 human tissues were compared and, as a result, a PCR product specifically expressed in pancreas was identified. This was named TSA305.

This product was composed of 371 nucleotides. Comparison of the data on this nucleotide with the DNA sequences occurring in the GenBank/EMBL data base using the FASTA program (Person, W. R., et al., Proc. Natl. Acad. Sci. USA, 85: 2444–2448 (1988)) revealed that this PCR product has no homology with any of other known DNA sequences.

(1-3) cDNA Screening

A human normal pancreas cDNA library was constructed using oligo(dT)+random hexamer-primed human normal pancreas cDNA and Uni-ZAP™ XR (product of Stratagene). The total of 1×10$_6$ clones were isolated by the method mentioned above and subjected to screening using a [$\Delta$-$^{33}$P ]-dCTP-labeled cDNA fragment. Positive clones were selected and the insert cDNA portions thereof were excised in vivo in pBluescript II SK(−).

As a result, about 100 plaques were identified as corresponding to TSA305. Based on this result, the percent transcription among all RNAs was calculated to be about 0.01%. The assembled cDNA sequence (TSA305) homologous with TSA305 comprises 7,885 nucleotides containing an open reading frame of 2,382 nucleotides coding for a protein composed of 794 amino acid residues with a calculated molecular weight of 88,768 Da.

Based on the primary sequence, it was revealed that this gene product (TSA305 protein) is a protein containing a fibronectin type II collagen binding domain.

The locus thereof was found to be q24.3-q31.1 on the 14th chromosome where a gene causative of insulin-dependent diabetes mellitus (IDDM) is considered to exist.

The TSA305 gene of the present invention showed a high level of homology with the nematode sel-1.

(2) Expression in Tissues

For checking the expression profiles of TSA305 in tissues, northern blot analysis was carried out using various human tissues.

For the northern blot analysis, human MTN (Multiple Tissue Northern) blots I and II (products of Clontech) were used. The cDNA fragments were labeled with [$\alpha$-$^{33}$P]-dCTP by PCR using a set of primers with T3 and T7 promoter sequences. The amplification product-containing membrane was prehybridized (the conditions were as indicated in the product protocol), followed by hybridization according to the product protocol.

After hybridization, the membrane was washed and exposed to an autoradiograph at −80° C. for 24 hours. The results are shown in FIG. 1.

In the figure, the human tissues used were heart, brain, placenta, lung, liver, skeletal muscle, kidney, pancreas, spleen, thymus, prostate, testis, ovary, small intestine, colon and peripheral blood leukocytes.

In the figure, a transcript homologous with TSA305 was observed specifically in the pancreas.

(3) FISH

FISH was carried out for chromosome arrangement according to a known method (Takahashi, E., et al., Hum. Genet., 86: 14–16 (1990)) using 0.5 μg of each cosmide DNA as a probe. FISH was detected with a Provia 100 film (product of Fuji, ISO 100) or a CCD camera system (Applied Imaging, product of Sightvision).

As a result, the signals obtained by testing 100 typical cells at (pro)metaphase by R banding were found localized on the bands q24.3-q31.1 of the 14th chromosome. Therefore, the locus of localization of the TSA305 on the chromosome could be identified as 14q24.3-q31.1.

(4) Expression of Transcript in Pancreatic Carcinoma Cell Lines and in Pancreatic Carcinoma Tissues as Revealed by RT-PCR Analysis To check whether the expression of the TSA305 gene varies in human pancreatic carcinoma cell lines and pancreatic carcinoma tissues, four cell lines (Aspc1 (metastatic adenocarcinoma; J. Natl. Cancer Inst., 67: 563–569 (1981)), Bxpc3 (adenocarcinoma, undifferentiated; Cancer Invest., 4: 15–23 (1986)), MiaPaca2 (adenocarcinoma; Int. J. Cancer, 19: 128–135 (1977)) and PANC1 (epithelioid, pancreatic duct carcinoma; Int. J. Cancer, 15: 741–747 (1975)) and 9 pancreatic carcinoma tissues (gifts from Dr. Nakamura at the University of Tokyo Institute of Medical Sciences) were subjected to RT-PCR analysis.

Thus, 10 μl of the total RNA isolated from each cell line or pancreatic carcinoma tissue using ISOGEN (product of Wako) was treated with 10 units of RNase-free DNase I (product of Boehringer Mannheim) for 15 minutes, followed by two repetitions of extraction with phenol-chloroform and precipitation with ethanol. The single-stranded cDNA was synthesized using Superscript I™ RNase H reverse transcriptase (product of Life Technology) with oligo-d(T) and random primers. A 2-μl portion of each product was used for PCR amplification.

The primers P1 and P2S having the nucleotide sequences shown under SEQ ID NO:5 and SEQ ID NO:6, respectively, were used in 25 cycles of PCR amplification.

The PCR reaction was carried out in 20 μl of a solution containing 25 ng of cDNA, 10 μM each primer, 2.5 mM dNTP and 0.25 U of Extaq DNA polymerase (product of Takara). Each PCR product was dissolved in 1.5% agarose gel stained with ethidium bromide.

Figure 2:
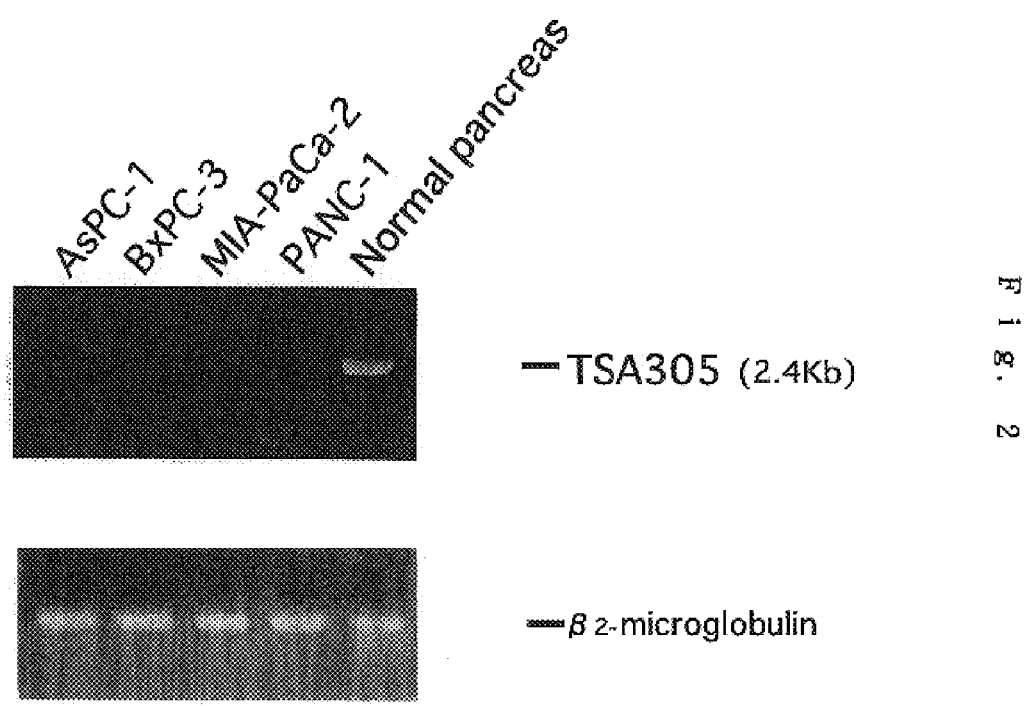
FIG. 2 is a photograph, in lieu of a drawing, illustrating the results of RT-PCR analysis of normal pancreatic cells and four cell lines as obtained in Example 1 (4). The results for TSA305 are shown in the upper section and the results for $\beta_2$-microglobulin as a control are shown in the lower section.

The four cell lines (lane 1=Aspc1; lane 2 =Bxpc3; lane 3=MiaPaca2; lane 4=PANC1) and a normal pancreatic tissue (normal pancreas, lane 5) were analyzed by RT-PCR in the above manner. The results are as shown in FIG. 2. The results for TSA305 are shown in the upper section and the results for $\mu_2$-microglobulin as a control are shown in the lower section.

From the figure, it was found that the expression of TSA305 is not detected in any of cancer tissues but is detected only in normal pancreatic tissues (cf. lane 5).

(5) Expression of the TSA305 Gene in Pancreatic Carcinoma (RT-PCR)

The expression of the TSA305 gene was checked in pancreatic carcinoma patient-derived samples (1T, 2T, 3T, 5T, 6T, 7T, 10T and 11T), pancreatic carcinoma (Tumor Pancreas) and normal pancreas (Invitrogen; Human Normal Pancreas) as well as a cancerous portion (23T) and a noncancerous portion (23N) of the same patient by the RT-PCR technique, as follows.

mRNA was extracted from each sample and the segment of 1581–2382 bp (801 base pairs) of TSA305 was amplified by RT-PCR and tested for detecting expression or no expression. As a concentration control, $\beta_2$-microglobulin was used. The results are shown in FIG. 3.

From the figure, reduced expression or lack of expression of the TSA305 gene was observed in all pancreatic carcinoma samples as compared with the normal pancreas.

INDUSTRIAL APPLICABILITY

According to the present invention, the novel pancreas-specific TSA305 gene and the protein encoded thereby are provided and, by utilizing these, a technology useful, among others, in elucidating, diagnosing, preventing and treating cancers, such as pancreatic carcinoma, or malignant transformation is provided.

What is claimed is:

1. An isolated polynucleotide which consists of a nucleotide sequence coding for a protein having the amino-acid sequence of SEQ ID NO:1.

2. The polynucleotide as claimed in claim 1, wherein said polynucleotide consists of the nucleotide sequence of SEQ ID NO:2.

3. An isolated polynucleotide selected from he group consisting of:

(a) a polynucleotide consisting of SEQ ID NO:5; and (b) a polynucleotide consisting of SEQ ID NO:6.

* * * * *

SEQUENCE LISTING

<160> NUMBER OF SEQ ID NOS: 6

<210> SEQ ID NO 1
<211> LENGTH: 794
<212> TYPE: PRT
<213> ORGANISM: Homo sapiens
<220> FEATURE:
<221> NAME/KEY: MISC_FEATURE
<223> OTHER INFORMATION: Human Normal Pancreas cDNA Library

<400> SEQUENCE: 1

Met Arg Val Arg Ile Gly Leu Thr Leu Leu Leu Cys Ala Val Leu Leu
1               5                   10                  15

Ser Leu Ala Ser Ala Ser Ser Asp Glu Glu Gly Ser Gln Asp Glu Ser
            20                  25                  30

Leu Asp Ser Lys Thr Thr Leu Thr Ser Asp Glu Ser Val Lys Asp His
        35                  40                  45

Thr Thr Ala Gly Arg Val Val Ala Gly Gln Ile Phe Leu Asp Ser Glu

-continued

```
                50                  55                  60
Glu Ser Glu Leu Glu Ser Ser Ile Gln Glu Glu Asp Ser Leu Lys
 65                  70                  75                  80

Ser Gln Glu Gly Glu Ser Val Thr Glu Asp Ile Ser Phe Leu Glu Ser
                 85                  90                  95

Pro Asn Pro Glu Asn Lys Asp Tyr Glu Glu Pro Lys Lys Val Arg Lys
                100                 105                 110

Pro Ala Leu Thr Ala Ile Glu Gly Thr Ala His Gly Glu Pro Cys His
                115                 120                 125

Phe Pro Phe Leu Phe Leu Asp Lys Glu Tyr Asp Glu Cys Thr Ser Asp
                130                 135                 140

Gly Arg Glu Asp Gly Arg Leu Trp Cys Ala Thr Thr Tyr Asp Tyr Lys
145                 150                 155                 160

Ala Asp Glu Lys Trp Gly Phe Cys Glu Thr Glu Glu Ala Ala Lys
                165                 170                 175

Arg Arg Gln Met Gln Glu Ala Glu Met Met Tyr Gln Thr Gly Met Lys
                180                 185                 190

Ile Leu Asn Gly Ser Asn Lys Lys Ser Gln Lys Arg Glu Ala Tyr Arg
                195                 200                 205

Tyr Leu Gln Lys Ala Ala Ser Met Asn His Thr Lys Ala Leu Glu Arg
                210                 215                 220

Val Ser Tyr Ala Leu Leu Phe Gly Asp Tyr Leu Pro Gln Asn Ile Gln
225                 230                 235                 240

Ala Ala Arg Glu Met Phe Glu Lys Leu Thr Glu Glu Gly Ser Pro Lys
                245                 250                 255

Gly Gln Thr Ala Leu Gly Phe Leu Tyr Ala Ser Gly Leu Gly Val Asn
                260                 265                 270

Ser Ser Gln Ala Lys Ala Leu Val Tyr Tyr Thr Phe Gly Ala Leu Gly
                275                 280                 285

Gly Asn Leu Ile Ala His Met Val Leu Gly Tyr Arg Tyr Trp Ala Gly
                290                 295                 300

Ile Gly Val Leu Gln Ser Cys Glu Ser Ala Leu Thr His Tyr Arg Leu
305                 310                 315                 320

Val Ala Asn His Val Ala Ser Asp Ile Ser Leu Thr Gly Gly Ser Val
                325                 330                 335

Val Gln Arg Ile Arg Leu Pro Asp Glu Val Glu Asn Pro Gly Met Asn
                340                 345                 350

Ser Gly Met Leu Glu Glu Asp Leu Ile Gln Tyr Tyr Gln Phe Leu Ala
                355                 360                 365

Glu Lys Gly Asp Val Gln Ala Gln Val Gly Leu Gly Gln Leu His Leu
                370                 375                 380

His Gly Gly Arg Gly Val Glu Gln Asn His Gln Arg Ala Phe Asp Tyr
385                 390                 395                 400

Phe Asn Leu Ala Ala Asn Ala Gly Asn Ser His Ala Met Ala Phe Leu
                405                 410                 415

Gly Lys Met Tyr Ser Glu Gly Ser Asp Ile Val Pro Gln Ser Asn Glu
                420                 425                 430

Thr Ala Leu His Tyr Phe Lys Lys Ala Ala Asp Met Gly Asn Pro Val
                435                 440                 445

Gly Gln Ser Gly Leu Gly Met Ala Tyr Leu Tyr Gly Arg Gly Val Gln
                450                 455                 460

Val Asn Tyr Asp Leu Ala Leu Lys Tyr Phe Gln Lys Ala Ala Glu Gln
465                 470                 475                 480
```

```
Gly Trp Val Asp Gly Gln Leu Gln Leu Gly Ser Met Tyr Tyr Asn Gly
                485                 490                 495
Ile Gly Val Lys Arg Asp Tyr Lys Gln Ala Leu Lys Tyr Phe Asn Leu
            500                 505                 510
Ala Ser Gln Gly Gly His Ile Leu Ala Phe Tyr Asn Leu Ala Gln Met
        515                 520                 525
His Ala Ser Gly Thr Gly Val Met Arg Ser Cys His Thr Ala Val Glu
    530                 535                 540
Leu Phe Lys Asn Val Cys Glu Arg Gly Arg Trp Ser Glu Arg Leu Met
545                 550                 555                 560
Thr Ala Tyr Asn Ser Tyr Lys Asp Gly Asp Tyr Asn Ala Ala Val Ile
                565                 570                 575
Gln Tyr Leu Leu Ala Glu Gln Gly Tyr Glu Val Ala Gln Ser Asn
            580                 585                 590
Ala Ala Phe Ile Leu Asp Gln Arg Glu Ala Ser Ile Val Gly Glu Asn
        595                 600                 605
Glu Thr Tyr Pro Arg Ala Leu Leu His Trp Asn Arg Ala Ala Ser Gln
    610                 615                 620
Gly Tyr Thr Val Ala Arg Ile Lys Leu Gly Asp Tyr His Phe Tyr Gly
625                 630                 635                 640
Phe Gly Thr Asp Val Asp Tyr Glu Thr Ala Phe Ile His Tyr Arg Leu
                645                 650                 655
Ala Ser Glu Gln Gln His Ser Ala Gln Ala Met Phe Asn Leu Gly Tyr
            660                 665                 670
Met His Glu Lys Gly Leu Gly Ile Lys Gln Asp Ile His Leu Ala Lys
        675                 680                 685
Arg Phe Tyr Asp Met Ala Ala Glu Ala Ser Pro Asp Ala Gln Val Pro
    690                 695                 700
Val Phe Leu Ala Leu Cys Lys Leu Gly Val Val Tyr Phe Leu Gln Tyr
705                 710                 715                 720
Ile Arg Glu Thr Asn Ile Arg Asp Met Phe Thr Gln Leu Asp Met Asp
                725                 730                 735
Gln Leu Leu Gly Pro Glu Trp Asp Leu Tyr Leu Met Thr Ile Ile Ala
            740                 745                 750
Leu Leu Leu Gly Thr Val Ile Ala Tyr Arg Gln Arg Gln His Gln Asp
        755                 760                 765
Met Pro Ala Pro Arg Pro Pro Gly Pro Arg Pro Ala Pro Pro Gln Gln
    770                 775                 780
Glu Gly Pro Pro Glu Gln Gln Pro Pro Gln
785                 790

<210> SEQ ID NO 2
<211> LENGTH: 2382
<212> TYPE: DNA
<213> ORGANISM: Homo sapiens
<220> FEATURE:
<221> NAME/KEY: misc_feature
<223> OTHER INFORMATION: Human Normal Pancreas cDNA Library

<400> SEQUENCE: 2
atgcgggtcc ggatagggct gacgctgctg ctgtgtgcgg tgctgctgag cttggcctcg      60
gcgtcctcgg atgaagaagg cagccaggat gaatccttag attccaagac tactttgaca     120
tcagatgagt cagtaaagga ccatactact gcaggcagta tagttgctgg tcaaatattt     180
cttgattcag aagaatctga attagaatcc tctattcaag aagaggaaga cagcctcaag     240
```

```
agccaagagg gggaaagtgt cacagaagat atcagctttc tagagtctcc aaatccagaa      300
aacaaggact atgaagagcc aagaaagta cggaaaccag ctttgaccgc cattgaaggc       360
acagcacatg gggagccctg ccacttccct tttcttttcc tagataagga gtatgatgaa      420
tgtacatcag atgggaggga gatggcaga ctgtggtgtg ctacaaccta tgactacaaa       480
gcagatgaaa agtggggctt ttgtgaaact gaagaagagg ctgctaagag acggcagatg      540
caggaagcag aaatgatgta tcaaactgga atgaaaatcc ttaatggaag caataagaaa     600
agccaaaaaa gagaagcata tcggtatctc caaaaggcag caagcatgaa ccataccaaa     660
gccctggaga gagtgtcata tgctcttta tttggtgatt acttgccaca gaatatccag      720
gcagcgagag agatgtttga gaagctgact gaggaaggct ctcccaaggg acagactgct     780
cttggctttc tgtatgcctc tggacttggt gttaattcaa gtcaggcaaa ggctcttgta     840
tattatacat ttggagctct tgggggcaat ctaatagccc acatggtttt gggttacaga     900
tactgggctg gcatcggcgt cctccagagt tgtgaatctg ccctgactca ctatcgtctt     960
gttgccaatc atgttgctag tgatatctcg ctaacaggag gctcagtagt acagagaata    1020
cggctgcctg atgaagtgga aaatccagga atgaacagtg gaatgctaga gaagatttg    1080 attcaatatt accagttcct agctgaaaaa ggtgatgtac aagcacaggt tggtcttgga    1140
caactgcacc tgcacggagg gcgtggagta gaacagaatc atcagagagc atttgactac    1200
ttcaatttag cagcaaatgc tggcaattca catgccatgg ccttttggg aaagatgtat    1260 tcggaaggaa gtgacattgt acctcagagt aatgagacag ctctccacta ctttaagaaa    1320
gctgctgaca tgggcaaccc agttggacag agtgggcttg gaatggccta cctctatggg    1380
agaggagttc aagttaatta tgatctagcc cttaagtatt tccagaaagc tgctgaacaa    1440
ggctgggtgg atgggcagct acagcttggt tccatgtact ataatggcat tggagtcaag    1500
agagattata acaggccttt gaagtatttt aatttagctt ctcagggagg ccatatcttg    1560
gctttctata acctagctca gatgcatgcc agtggcaccg gcgtgatgcg atcatgtcac    1620
actgcagtgg agttgtttaa gaatgtatgt gaacgaggcc gttggtctga aaggcttatg    1680
actgcctata acagctataa agatggcgat tacaatgctg cagtgatcca gtacctcctc    1740
ctggctgaac agggctatga agtggcacaa agcaatgcag cctttattct tgatcagaga    1800
gaagcaagca ttgtaggtga gaatgaaact tatcccagag ctttgctaca ttggaacagg    1860
gccgcctctc aaggctatac tgtggctaga attaagctcg gagactacca tttctatggg    1920
tttggcaccg atgtagatta tgaaactgca tttattcatt accgtctggc ttctgagcag    1980
caacacagtg cacaagctat gtttaatctg ggatatatgc atgagaaagg actgggcatt    2040
aaacaggata ttcaccttgc gaaacgtttt tatgacatgg cagctgaagc cagcccagat    2100
gcacaagttc cagtcttcct agccctctgc aaattgggcg tcgtctattt cttgcagtac    2160
atacgggaaa caaacattcg agatatgttc acccaacttg atatggacca gcttttggga    2220
cctgagtggg acctttacct catgaccatc attgcgctgc tgttgggaac agtcatagct    2280
tacaggcaaa ggcagcacca agacatgcct gcacccaggc ctccagggcc acggccagct    2340
ccaccccagc aggaggggcc accagagcag cagccaccac ag                      2382
```

<210> SEQ ID NO 3
<211> LENGTH: 7885
<212> TYPE: DNA
<213> ORGANISM: Homo sapiens
<220> FEATURE:

-continued

```
<221> NAME/KEY: exon
<222> LOCATION: (46)..(2427)
<221> NAME/KEY: misc_feature
<223> OTHER INFORMATION: Human Normal Pancreas cDNA Library

<400> SEQUENCE: 3
gcgaaggcga cagctctagg ggttggcacc ggccccgaga ggagg atg cgg gtc cgg      57
                                                Met Arg Val Arg
                                                  1 ata ggg ctg acg ctg ctg ctg tgt gcg gtg ctg ctg agc ttg gcc tcg      105
Ile Gly Leu Thr Leu Leu Leu Cys Ala Val Leu Leu Ser Leu Ala Ser
  5              10                  15                  20 gcg tcc tcg gat gaa gaa ggc agc cag gat gaa tcc tta gat tcc aag      153
Ala Ser Ser Asp Glu Glu Gly Ser Gln Asp Glu Ser Leu Asp Ser Lys
             25                  30                  35 act act ttg aca tca gat gag tca gta aag gac cat act act gca ggc      201
Thr Thr Leu Thr Ser Asp Glu Ser Val Lys Asp His Thr Thr Ala Gly
         40                  45                  50 aga gta gtt gct ggt caa ata ttt ctt gat tca gaa gaa tct gaa tta      249
Arg Val Val Ala Gly Gln Ile Phe Leu Asp Ser Glu Glu Ser Glu Leu
     55                  60                  65 gaa tcc tct att caa gaa gag gaa gac agc ctc aag agc caa gag ggg      297
Glu Ser Ser Ile Gln Glu Glu Glu Asp Ser Leu Lys Ser Gln Glu Gly
 70                  75                  80 gaa agt gtc aca gaa gat atc agc ttt cta gag tct cca aat cca gaa      345
Glu Ser Val Thr Glu Asp Ile Ser Phe Leu Glu Ser Pro Asn Pro Glu
 85                  90                  95                 100 aac aag gac tat gaa gag cca aag aaa gta cgg aaa cca gct ttg acc      393
Asn Lys Asp Tyr Glu Glu Pro Lys Lys Val Arg Lys Pro Ala Leu Thr
                105                 110                 115 gcc att gaa ggc aca gca cat ggg gag ccc tgc cac ttc cct ttt ctt      441
Ala Ile Glu Gly Thr Ala His Gly Glu Pro Cys His Phe Pro Phe Leu
            120                 125                 130 ttc cta gat aag gag tat gat gaa tgt aca tca gat ggg agg gaa gat      489
Phe Leu Asp Lys Glu Tyr Asp Glu Cys Thr Ser Asp Gly Arg Glu Asp
        135                 140                 145 ggc aga ctg tgg tgt gct aca acc tat gac tac aaa gca gat gaa aag      537
Gly Arg Leu Trp Cys Ala Thr Thr Tyr Asp Tyr Lys Ala Asp Glu Lys
    150                 155                 160 tgg ggc ttt tgt gaa act gaa gaa gag gct gct aag aga cgg cag atg      585
Trp Gly Phe Cys Glu Thr Glu Glu Glu Ala Ala Lys Arg Arg Gln Met
165                 170                 175                 180 cag gaa gca gaa atg atg tat caa act gga atg aaa atc ctt aat gga      633
Gln Glu Ala Glu Met Met Tyr Gln Thr Gly Met Lys Ile Leu Asn Gly
                185                 190                 195 agc aat aag aaa agc caa aaa aga gaa gca tat cgg tat ctc caa aag      681
Ser Asn Lys Lys Ser Gln Lys Arg Glu Ala Tyr Arg Tyr Leu Gln Lys
            200                 205                 210 gca gca agc atg aac cat acc aaa gcc ctg gag aga gtg tca tat gct      729
Ala Ala Ser Met Asn His Thr Lys Ala Leu Glu Arg Val Ser Tyr Ala
        215                 220                 225 ctt tta ttt ggt gat tac ttg cca cag aat atc cag gca gcg aga gag      777
Leu Leu Phe Gly Asp Tyr Leu Pro Gln Asn Ile Gln Ala Ala Arg Glu
    230                 235                 240 atg ttt gag aag ctg act gag gaa ggc tct ccc aag gga cag act gct      825
Met Phe Glu Lys Leu Thr Glu Glu Gly Ser Pro Lys Gly Gln Thr Ala
245                 250                 255                 260 ctt ggc ttt ctg tat gcc tct gga ctt ggt gtt aat tca agt cag gca      873
Leu Gly Phe Leu Tyr Ala Ser Gly Leu Gly Val Asn Ser Ser Gln Ala
                265                 270                 275
```

-continued

| | | |
|---|---|---|
| aag gct ctt gta tat tat aca ttt gga gct ctt ggg ggc aat cta ata<br>Lys Ala Leu Val Tyr Tyr Thr Phe Gly Ala Leu Gly Gly Asn Leu Ile<br>             280                       285                     290 | 921 |
| gcc cac atg gtt ttg ggt tac aga tac tgg gct ggc atc ggc gtc ctc<br>Ala His Met Val Leu Gly Tyr Arg Tyr Trp Ala Gly Ile Gly Val Leu<br>        295                       300                    305 | 969 |
| cag agt tgt gaa tct gcc ctg act cac tat cgt ctt gtt gcc aat cat<br>Gln Ser Cys Glu Ser Ala Leu Thr His Tyr Arg Leu Val Ala Asn His<br>310                       315                    320 | 1017 |
| gtt gct agt gat atc tcg cta aca gga ggc tca gta gta cag aga ata<br>Val Ala Ser Asp Ile Ser Leu Thr Gly Gly Ser Val Val Gln Arg Ile<br>325                       330                    335                    340 | 1065 |
| cgg ctg cct gat gaa gtg gaa aat cca gga atg aac agt gga atg cta<br>Arg Leu Pro Asp Glu Val Glu Asn Pro Gly Met Asn Ser Gly Met Leu<br>                       345                    350                    355 | 1113 |
| gaa gaa gat ttg att caa tat tac cag ttc cta gct gaa aaa ggt gat<br>Glu Glu Asp Leu Ile Gln Tyr Tyr Gln Phe Leu Ala Glu Lys Gly Asp<br>               360                    365                    370 | 1161 |
| gta caa gca cag gtt ggt ctt gga caa ctg cac ctg cac gga ggg cgt<br>Val Gln Ala Gln Val Gly Leu Gly Gln Leu His Leu His Gly Gly Arg<br>375                       380                    385 | 1209 |
| gga gta gaa cag aat cat cag aga gca ttt gac tac ttc aat tta gca<br>Gly Val Glu Gln Asn His Gln Arg Ala Phe Asp Tyr Phe Asn Leu Ala<br>390                       395                    400 | 1257 |
| gca aat gct ggc aat tca cat gcc atg gcc ttt ttg gga aag atg tat<br>Ala Asn Ala Gly Asn Ser His Ala Met Ala Phe Leu Gly Lys Met Tyr<br>405                       410                    415                    420 | 1305 |
| tcg gaa gga agt gac att gta cct cag agt aat gag aca gct ctc cac<br>Ser Glu Gly Ser Asp Ile Val Pro Gln Ser Asn Glu Thr Ala Leu His<br>                       425                    430                    435 | 1353 |
| tac ttt aag aaa gct gct gac atg ggc aac cca gtt gga cag agt ggg<br>Tyr Phe Lys Lys Ala Ala Asp Met Gly Asn Pro Val Gly Gln Ser Gly<br>               440                    445                    450 | 1401 |
| ctt gga atg gcc tac ctc tat ggg aga gga gtt caa gtt aat tat gat<br>Leu Gly Met Ala Tyr Leu Tyr Gly Arg Gly Val Gln Val Asn Tyr Asp<br>455                       460                    465 | 1449 |
| cta gcc ctt aag tat ttc cag aaa gct gct gaa caa ggc tgg gtg gat<br>Leu Ala Leu Lys Tyr Phe Gln Lys Ala Ala Glu Gln Gly Trp Val Asp<br>470                       475                    480 | 1497 |
| ggg cag cta cag ctt ggt tcc atg tac tat aat ggc att gga gtc aag<br>Gly Gln Leu Gln Leu Gly Ser Met Tyr Tyr Asn Gly Ile Gly Val Lys<br>485                       490                    495                    500 | 1545 |
| aga gat tat aaa cag gcc ttg aag tat ttt aat tta gct tct cag gga<br>Arg Asp Tyr Lys Gln Ala Leu Lys Tyr Phe Asn Leu Ala Ser Gln Gly<br>                       505                    510                    515 | 1593 |
| ggc cat atc ttg gct ttc tat aac cta gct cag atg cat gcc agt ggc<br>Gly His Ile Leu Ala Phe Tyr Asn Leu Ala Gln Met His Ala Ser Gly<br>520                       525                    530 | 1641 |
| acc ggc gtg atg cga tca tgt cac act gca gtg gag ttg ttt aag aat<br>Thr Gly Val Met Arg Ser Cys His Thr Ala Val Glu Leu Phe Lys Asn<br>               535                    540                    545 | 1689 |
| gta tgt gaa cga ggc cgt tgg tct gaa agg ctt atg act gcc tat aac<br>Val Cys Glu Arg Gly Arg Trp Ser Glu Arg Leu Met Thr Ala Tyr Asn<br>550                       555                    560 | 1737 |
| agc tat aaa gat ggc gat tac aat gct gca gtg atc cag tac ctc ctc<br>Ser Tyr Lys Asp Gly Asp Tyr Asn Ala Ala Val Ile Gln Tyr Leu Leu<br>565                       570                    575                    580 | 1785 |
| ctg gct gaa cag ggc tat gaa gtg gca caa agc aat gca gcc ttt att<br>Leu Ala Glu Gln Gly Tyr Glu Val Ala Gln Ser Asn Ala Ala Phe Ile<br>                       585                    590                    595 | 1833 |

```
ctt gat cag aga gaa gca agc att gta ggt gag aat gaa act tat ccc        1881
Leu Asp Gln Arg Glu Ala Ser Ile Val Gly Glu Asn Glu Thr Tyr Pro
        600                 605                 610 aga gct ttg cta cat tgg aac agg gcc gcc tct caa ggc tat act gtg        1929
Arg Ala Leu Leu His Trp Asn Arg Ala Ala Ser Gln Gly Tyr Thr Val
        615                 620                 625 gct aga att aag ctc gga gac tac cat ttc tat ggg ttt ggc acc gat        1977
Ala Arg Ile Lys Leu Gly Asp Tyr His Phe Tyr Gly Phe Gly Thr Asp
    630                 635                 640 gta gat tat gaa act gca ttt att cat tac cgt ctg gct tct gag cag        2025
Val Asp Tyr Glu Thr Ala Phe Ile His Tyr Arg Leu Ala Ser Glu Gln
645                 650                 655                 660 caa cac agt gca caa gct atg ttt aat ctg gga tat atg cat gag aaa        2073
Gln His Ser Ala Gln Ala Met Phe Asn Leu Gly Tyr Met His Glu Lys
                665                 670                 675 gga ctg ggc att aaa cag gat att cac ctt gcg aaa cgt ttt tat gac        2121
Gly Leu Gly Ile Lys Gln Asp Ile His Leu Ala Lys Arg Phe Tyr Asp
            680                 685                 690 atg gca gct gaa gcc agc cca gat gca caa gtc cca gtc ttc tta gcc        2169
Met Ala Ala Glu Ala Ser Pro Asp Ala Gln Val Pro Val Phe Leu Ala
        695                 700                 705 ctc tgc aaa ttg ggc gtc gtc tat ttc ttg cag tac ata cgg gaa aca        2217
Leu Cys Lys Leu Gly Val Val Tyr Phe Leu Gln Tyr Ile Arg Glu Thr
    710                 715                 720 aac att cga gat atg ttc acc caa ctt gat atg gac cag ctt ttg gga        2265
Asn Ile Arg Asp Met Phe Thr Gln Leu Asp Met Asp Gln Leu Leu Gly
725                 730                 735                 740 cct gag tgg gac ctt tac ctc atg acc atc att gcg ctg ctg ttg gga        2313
Pro Glu Trp Asp Leu Tyr Leu Met Thr Ile Ile Ala Leu Leu Leu Gly
                745                 750                 755 aca gtc ata gct tac agg caa agg cag cac caa gac atg cct gca ccc        2361
Thr Val Ile Ala Tyr Arg Gln Arg Gln His Gln Asp Met Pro Ala Pro
            760                 765                 770 agg cct cca ggg cca cgg cca gct cca ccc cag cag gag ggg cca cca        2409
Arg Pro Pro Gly Pro Arg Pro Ala Pro Pro Gln Gln Glu Gly Pro Pro
        775                 780                 785 gag cag cag cca cca cag taataggcac tgggtccagc cttgatcagt                2457
Glu Gln Gln Pro Pro Gln
    790 gacagcgaag gaagttatct gctgggaaca cttgcatttg atttaggacc ttggatcagt       2517 ggtcacctcc cagaagaggc acggcacaag gaagcattga attcctaaag ctgcttagaa       2577 tctgatgcct ttatttcag  ggataagtaa ctcttaccta aactgagctg aatgtttgtt       2637 tcagtgccat atggagtaac aactttcagt ggcttttttt tttcttttct ggaaacatat       2697 gtgagacact cagagtaatg tctactgtat ccagctatct ttctttggat ccttttggtc       2757 attatttcag tgtgcataag ttcttaatgt caaccatctt taaggtattg tgcatcgaca       2817 ctaaaaactg atcagtgtta aaaggaaaa  cccagttgca agtttaaacg tgttcgaaag       2877 tctgaaaata gaacttgcct tttaagttaa aaaaaaaaa  aaagctatct tgaaaatgtt       2937 ttggaactgc gataactgag aaacttctta ccagtccaca tgcaattaaa catattcagc       2997 atatttgtta tttaaaagg  gagggttggg aggtttctta ttggtgattg tcacacggta       3057 taccatactc ctctccttca aagaatgaaa ggccttgtta aggagttttt tgtgagcttt       3117 acttctttgg aatggaatat acttatgcaa aaccttgtga actgactcct tgcactaacg       3177 cgagtttgcc ccacctactc tgtaatttgc ttgtttgttt tgaatataac agagccttga       3237
```

```
tccagaagcc agaggatgga ctaagtggga gaaattagaa aacaaaacga actctggttg   3297
gggtactacg atcacagaca cagacatact tttcctaaag ttgaagcatt tgttcccagg   3357
atttatttta ctttgcattt cttttttgcac aaagaacaca tcaccttcct gaattcttta   3417
aatatgaaat atcattgcca gggtatggct tacagtgact actattatca atactaaaac   3477
tcagagaatc aaagatggat taaactcagt ggttgatgaa agccaaaacc tgtttgtact   3537
gttctatact attcaggtat cttttattt ctgatagttt tatattataa tagaaagcca   3597
gccactgctt agctatcata gtcaccattt tctcactgtt aacattagga aaatcaaggc   3657
tactatgctt caggattgtc tggttaaata gtatgggaaa aaaactgaag agtttcaaca   3717
taattacaca cgtgaaataa ttacagctta aactgaattt gtatttcatt ttattgtcag   3777
atggtggtgt tcaccagcct gtatcttgtc tgagactgca ttcgtatctg agcaggtttt   3837
ctatgcctac tgatgtcagt atgtttatac taaccttcat gcttttttcc cagaatccct   3897
catctgccag aaaacttgaa aagtttattg cttgtagagt tgtactgctt tgattttga   3957 agttggggta gtagttagaa ctagatttaa ctagtctata atgaacatga aggcttttat   4017
atatgaagtt gtatacctt ttgtgtttag agaattatgg gaaacctggt aagcaaaact   4077
ttcctcccag ataattgctt ccaaattcga agagttagtc accaagagag ccatatgtat   4137
gaaagcgtat ctgtgaaagg taggaaactt acccccccta agtgtaatgt tgctttaggc   4197
aactcttgta aatagtgaga cttgtttggt ctcttacatg tagagatttg agtgcagttg   4257
gtacagtact ttggtgtctc caccactgtc ccttctcccc gcttcaaaat aagtgtaatc   4317
cacggtagca gccacacttc cttcagaagg aactgttata atttatttaa aagttgaaaa   4377
accacccaag atgactacca actttcactt ttttttcttct gccatccacc ctcatttcc   4437 ctttagcaag attttttatat ctaactttcc ttccctccat tgagtacgtg ctttgagaaa   4497
acatttctta aaacagtgtg tgccacctaa ggctggatgg gaaagtgcag tcttgttgtt   4557
catataaaaa acacacttct tattagttta cccacttgcc ttttttctatt gttaatgttc   4617 tgaatttcct tttcttggct tgtttctact tcattttaac cctgggtcac ttgctgccag   4677
cagtttgtga atggtgtctt tcaaataact tagttcttat ggcttcactt aaagactgtc   4737
tcaaaaatac tttgctctct tcttctttt tgttcatggg acatggtacc taagcaaata   4797
ggagttgggt ttggtttttc tcctaaaata atgctcaata cttacctaat caaatggcat   4857
ccatttgaat aaaatgacaa taactaaagc tagttaatgt cagtgacatt aaactaactc   4917
caggattcag gagtttttaat gttagaattt agatttaaca gatagagtgt ggcttcattt   4977
gtccatggta gcccatctct cctaagacct tttctagtct gtcttcctgc cttcgaactt   5037
gatgacagta aaaccctgtt tagtattctc ttgtgcattt ggtttgttgg ttagccgact   5097
gtcttgaaac tattcatttt gcttctagtt ttattttaca gaggtagcat tggtgggttt   5157 ttttttttt ttctgtctct gtgtttgaag tttcagtttc tgttttctag gtaaggctta   5217 ttttttgatta gcagtcaatg gcaaagaaaa agtaaatcaa agatgacttc ttttcaaaat   5277
gtatggccct tttattgcac ttttaactca gatgaattta taaattatta atcttgatac   5337
taaggatttg ttactttttt gcatattagg ttaattttta ccttacatgt gagagtctta   5397
ccactaagcc attctgtctc tgtactgttg ggaagttttg gaaaccctg ccagtgatct   5457 ggtgatgatc tgatgattta tttaaagagc cgttgatgcc tccaggaaac ttaagtatt   5517 tattaatata tatataggaa ttttttttta ttttgctttg tctttctctc ccttctttta   5577
tcctcatgtt cattcttcaa accagtgttt tggaagtatg catgcaggcc tataaatgaa   5637
```

-continued

```
aaacacaatt ctttatgtgt atagcatgtg tattaatgtc taactacata cgcaaaaact    5697
tcctttacag aggttcggac taacatttca catgcacatt tcaaaacaag atgtgtcatg    5757
aaaacagccc ctttacctgc caagacaagc agggctatat ttcagtgaca gctggatatt    5817
ttgtttctga aagtgaatct cataatatat atatgtatta cacattatta tgactagaag    5877
tatgtaagaa atgatcagaa caaaagaaaa tttctatttt catgcaaata tttttcatca    5937
gtcatcactc tcaaatataa attaaaatat aacactcctg aatgcctgag cacgatctg     5997 gattttaaat gtgtggtatt cattgaaaag aagctctcca cccacttggt atttcaagaa    6057
aatttaaaac gatcccaagg aaagatgatt tgtatgttaa agtgactgca caagtaaaag    6117
tccaatgttg tgtgcatgaa aaggattcct tggttatgtg cagggaatca tctcacatgc    6177
tgtttttcct atttggtttg agaaacaggc tgacactatt ctctttgatt agaaaataaa    6237
ctcataaaac tcataatgtt gatataatca agatgttaac cactataaat atgtagaaga    6297
ggaagtttta aatagacctt aagctggcat tgtgaaggaa caccatggta gactcttttt    6357
ggtaatggta ttttgtattt aatgaaatgc agtataaagg ttggtgaagt gtaataataa    6417
ttgtgtaaac aaatcctgtt taatagaaga gatgtacaga atcgttttgg tactgtatct    6477
tgaaacttgt gaaataaaga ttccactttt ggttatcctg tatgctgtaa tataccacaa    6537
ccaagcaccc tttccagaca gacttttttt aagctgaatg aatccaattt tttaatgttt    6597 tttgaaatt cagaagcttc tgaaaacatt cacttgtggc aatttgaatt tatctttcat    6657
tttaaactcc tgaaattcag attttttacaa gtccaatatt gccctaggga gaacatgaat    6717
ttgctaagaa atgttatctt ttaaatctct gatatctttg tcttgaagca gccttgatat    6777
gtagtaagcg tgattcactt tagcctgatt ataatattat ttatctaaag tttgtttatg    6837
cattgccttg tcccaggaat ttttttaagag gacttgcaga gacacgtacc acacagtaac    6897
atttagacta aatatgctct gagtaaagga gaaatgaaaa aatattaaat caagagtgaa    6957
catgtacaca aagtgcaatt ggaagtgggc tacaaattta gcccccagct tcccagcagg    7017
caactcaaag aggtaactga ggtaaaatgt tccagctcag aagcattgga tcttggataa    7077
aaagcctaca tgatgcaaac tgtggcaact gagatgtcag atctcaagat ctcaaattgt    7137
acttgtggga gcacagtcag tgaccccaga tgaccttgac tgacctaaaa gttgtggggg    7197
aagtcggatg tcagagcctt aacaccagca ggtgaccatc caacctgggg caatgcctgc    7257
ctgttcacca cttagcctct ttctggcaag tcattagaat gtcctccatc ttcattggct    7317
gcaacttgat gagctacagc ctctttccta acttcctta tgatgctagt ttaggttggt     7377
tataccagct tggaagtatg cttagattaa gttacagcag atacacaaat tagatgcaag    7437
taaaaaaaat cagaatttct gtagtagaaa ctacgaaaaa taaaaggaa agttttact      7497 ttttgggtat ttttttacga ataagaaaaa gtgagcgtta atcagttcaa aaggaggtac    7557
tgctgtgtaa tgggctttgt acgttccttc tcatgtcact tacgtcacta cttcgccatc    7617
aaattgaaca agcttttaat tagatcctga aaattcacta tgctagtagt ttattggtag    7677
tattatattt tgagtagaac tctgattttc cctagaggcc aaattctttt tatctgggtt    7737 aatttcttt aaacataaca atgttaatgc tgaattgtat attaaatccc atttctaaaa      7797
accacacaat tttttctcat gtaagttgag tggaatgtgg ttagttaact gaatttggaa    7857
tgttcatata ataatttgt tgctgctc                                          7885
```

<210> SEQ ID NO 4

```
<211> LENGTH: 10
<212> TYPE: DNA
<213> ORGANISM: Artificial Sequence
<220> FEATURE:
<221> NAME/KEY: misc_feature
<223> OTHER INFORMATION: Primer Sequence for PCR of TSA305

<400> SEQUENCE: 4
gatctgacac                                                          10

<210> SEQ ID NO 5
<211> LENGTH: 28
<212> TYPE: DNA
<213> ORGANISM: Artificial Sequence
<220> FEATURE:
<221> NAME/KEY: misc_feature
<223> OTHER INFORMATION: Primer Sequence for PCR of TSA305

<400> SEQUENCE: 5
gatcggatcc aggaggatgc gggtccgg                                      28

<210> SEQ ID NO 6
<211> LENGTH: 30
<212> TYPE: DNA
<213> ORGANISM: Artificial Sequence
<220> FEATURE:
<221> NAME/KEY: misc_feature
<223> OTHER INFORMATION: Primer Sequence for PCR of TSA305

<400> SEQUENCE: 6
gatcctcgag ttactgtggt ggctgctgct                                    30
```